United States Patent
Gramoli

(10) Patent No.: US 12,427,331 B2
(45) Date of Patent: Sep. 30, 2025

(54) HANDPIECE FOR INTRAORIFICE RADIOFREQUENCY TREATMENTS

(71) Applicants: TARAS S.R.L., Bologna (IT); Roberta Mazzanti, Loiano (IT); Giorgio Maullu, Oristano (IT)

(72) Inventor: Pietro Tomaso Gramoli, Loiano (IT)

(73) Assignees: TARAS S.R.L., Bologna (IT); Roberta Mazzanti, Loiano (IT); Giorgio Maullu, Oristano (IT)

( * ) Notice: Subject to any disclaimer, the term of this patent is extended or adjusted under 35 U.S.C. 154(b) by 780 days.

(21) Appl. No.: 17/287,669

(22) PCT Filed: Oct. 23, 2018

(86) PCT No.: PCT/IT2018/000136
§ 371 (c)(1),
(2) Date: Apr. 22, 2021

(87) PCT Pub. No.: WO2020/084645
PCT Pub. Date: Apr. 30, 2020

(65) Prior Publication Data
US 2021/0393970 A1    Dec. 23, 2021

(51) Int. Cl.
*A61N 1/40*    (2006.01)
(52) U.S. Cl.
CPC .................... *A61N 1/403* (2013.01)
(58) Field of Classification Search
CPC ...................................... A61N 1/403
See application file for complete search history.

(56) References Cited

U.S. PATENT DOCUMENTS

2014/0148878 A1    5/2014    Khatri
2016/0135876 A1*   5/2016    Parmer ............ A61B 18/1233
                                                              606/41

FOREIGN PATENT DOCUMENTS

| CN | 102971047 A | 3/2013 |
| EP | 2477695 A2 | 7/2012 |
| EP | 3207892 A1 | 8/2017 |
| WO | 9819613 A1 | 5/1998 |
| WO | 2011034986 A2 | 3/2011 |

OTHER PUBLICATIONS

International Search Report issued Aug. 5, 2019 re: Application No. PCT/IT2018/000136, pp. 1-3, citing: WO 2011/034986 A2, WO 98/19613 A and US 2014/0148878 A1.
Written Opinion issued Aug. 5, 20219 re: Application No. PCT/IT2018/000136, pp. 1-3, citing: WO 2011/034986 A2, WO 98/19613 A1 and US 2014/0148878 A1.
Chinese Office Action for Application No. 201880098939.2, dated Dec. 26, 2023, 17 pages with translation.
Chinese Office Action for Application No. 201880098939.2, dated Jun. 4, 2024, 12 pages with translation.

* cited by examiner

*Primary Examiner* — Kaitlyn E Smith
(74) *Attorney, Agent, or Firm* — CANTOR COLBURN LLP

(57) ABSTRACT

A handpiece for intraorifice radiofrequency treatments of the type including a substantially tubular body provided with at least one emitter along its outer surface. The at least one emitter is connected by cables to at least one power supply unit.

8 Claims, 2 Drawing Sheets

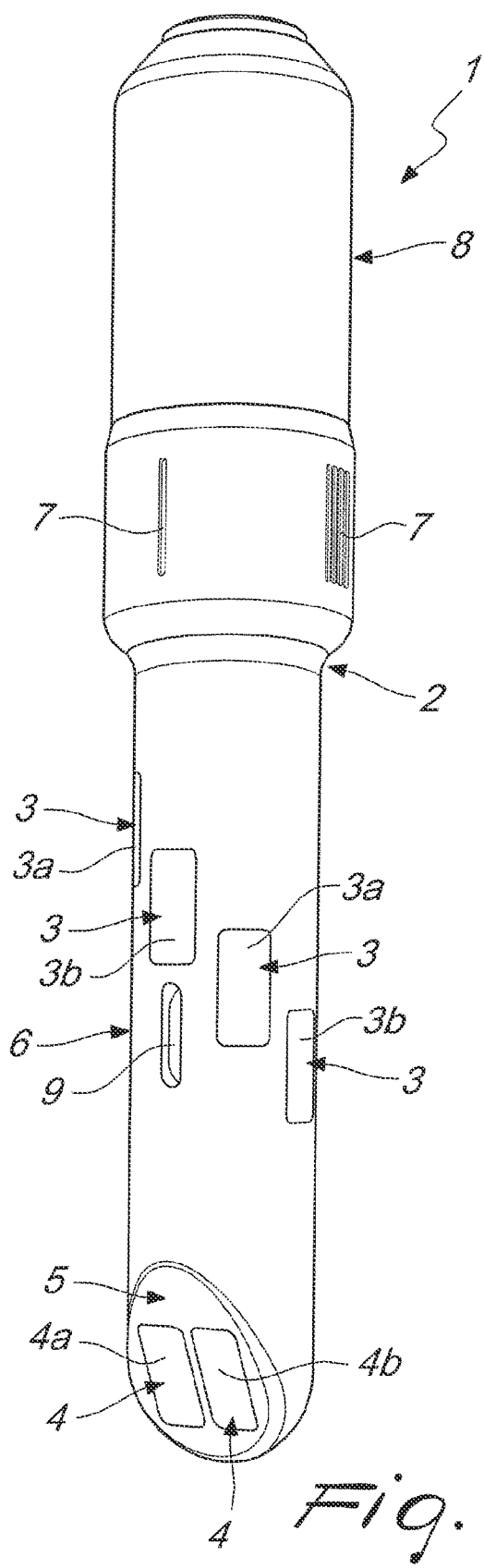
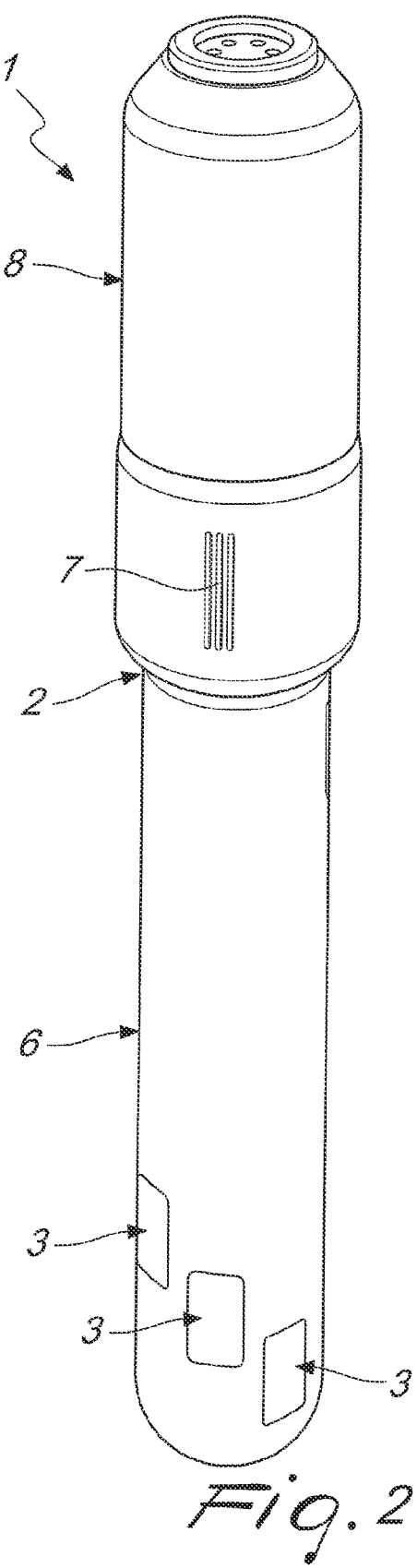

HANDPIECE FOR INTRAORIFICE RADIOFREQUENCY TREATMENTS

TECHNICAL FIELD

The present disclosure relates to a handpiece for intraorifice radiofrequency treatments; in particular, the handpiece is indicated for the execution of treatments of the vagina of an aesthetic nature, for tissue rejuvenation and medical treatment, for treating some specific pathologies of the urogenital system.

BACKGROUND

Radiofrequency aesthetic/medical therapy utilizes the effect generated by adapted medical devices, which causes a noninvasive "reshaping" of the tissues, with an action that is particularly effective in contrasting skin relaxation of the face and of the body.

The principle underlying radiofrequency is to generate a thermal is shock in the deepest layers of the skin in order to trigger a regenerative response by the body. Radiofrequency application causes the deep layers of the skin to reach temperatures close to or higher than 40° C., at the same time keeping the epidermis at lower temperatures so that it remains protected throughout the treatment.

This entails an immediate distension of the collagen fibers, a stimulation of fibroblasts to produce new collagen, a release of cytokines and a regeneration of the matrix, reduction of the contractility of facial mimetic muscles and a decrease in the percentage of peroxide radicals, with a consequent antioxidant topical effect.

The radiofrequency electromagnetic field is generated by a high-frequency electrical alternating current (over 100 kHz), the flow of which changes very rapidly and which does not stimulate the nerve and muscle tissue but has a controlled "thermal effect" due to the increase in the temperature of the dermis.

The biophysical effect of radiofrequency is in fact based on the conversion of electrical energy into heat: heating occurs as a consequence of the molecular oscillation caused by a rotational displacement of the intracellular electrolytes.

The application of radiofrequency is being extended to several and distinct treatment types and recently devices for the reshaping and rejuvenation of the tissues of the vagina and of the related tissues are becoming widespread.

It is known, from the contents of EP2477695, to resort to a handpiece for radiofrequency treatments that allows to provide effective treatments also of the internal walls of the vagina, in particular on the mucous membranes and on the epithelial tissues.

The handpiece according to EP2477695 comprises a terminal head made of electrically conducting material, through which it is possible to deliver a flow of energy onto the tissues with which it makes contact. This is solution therefore has a first problem in relation to the need to place the head in direct contact with the tissues.

This means that at the end of each treatment (or in any case before the subsequent treatment) it is necessary to perform operations for the sterilization and sanitizing of the head (and of the handpiece parts that are proximate thereto), since said head has come into direct contact with the mucous membranes of a patient (with consequent possible risks of cross-contamination if sterilization were not performed).

These operations are expensive and render said head unusable for a certain time interval: the operator, therefore, must have a number of heads that is sufficient to perform multiple distinct treatments in sequence (the provisioning of several heads contributes to increase the operating costs of the handpiece described in EP2477695).

EP2477695 describes a handpiece for radiofrequency treatments of the resistive type: this type of treatment entails an intense heating of the tissues of the patient that are coupled to the transducer, and for this reason cooling means are adopted which remove heat from it, avoiding overheating of the treated tissues.

The adoption of cooling means entails an increase in the costs of the handpiece and a higher constructive complication thereof, furthermore increasing the likelihood of a malfunction correlated indeed to cooling.

Finally, the handpiece according to EP2477695 imposes on the operator a use according to specific procedures and complex movement sequences, in order to make the head face each portion of the epithelial tissue to be treated for a predefined time.

SUMMARY

The aim of the present disclosure is to solve the problems described above, providing a handpiece for intraorifice radiofrequency treatments that can avoid phenomena of cross-contamination among multiple patients and is therefore very hygienic and safe.

Within this aim, the disclosure provides a handpiece for intraorifice radiofrequency treatments that does not require the presence of components that are expensive to replace at each treatment.

The disclosure further provides a handpiece for intraorifice radiofrequency treatments that does not require means for cooling the component that supplies current with the correct electrical parameters to the head.

The disclosure also provides a handpiece for intraorifice radiofrequency treatments that is scarcely subject to malfunctions in relation to the minimum number of components that constitute it and is therefore extremely reliable.

The disclosure proposes a handpiece for intraorifice radiofrequency treatments that is very simple to use and can be used even by operators who are not specifically trained although they are professionally authorized.

The present disclosure further provides a handpiece for intraorifice radiofrequency treatments that has low costs, is relatively simple to provide and is safe in application.

This aim and these advantages are achieved by providing a handpiece for intraorifice radiofrequency treatments of the type comprising a substantially tubular body provided with at least one emitter along its outer surface, said at least one emitter being connected by means of adapted cables to at least one power supply unit provided with devices for the control and management of the electrical values transmitted to said at least one emitter, characterized in that it comprises, distributed on the outer surface of the tubular body made of dielectric material, at least two emitters which comprise at least one electrode surmounted by a layer made of insulating material constituted by the dielectric element of a ceramic capacitor, one surface of said element comprising a cladding made of a material with high electrical conductivity which is electrically connected to said electrode for the dispensing of a radiofrequency treatment of the capacitive type.

BRIEF DESCRIPTION OF THE DRAWINGS

Further characteristics and advantages of the disclosure will become better apparent from the description of a preferred but not exclusive embodiment of the handpiece for intraorifice radiofrequency treatments according to the disclosure, illustrated by way of nonlimiting example in the accompanying drawings, wherein:

FIG. 1 is a schematic perspective view of a handpiece for intraorifice radiofrequency treatments according to the disclosure;

FIG. 2 is a schematic perspective view of the handpiece of FIG. 1 from another viewpoint.

DETAILED DESCRIPTION OF THE DRAWINGS

Figure 3:
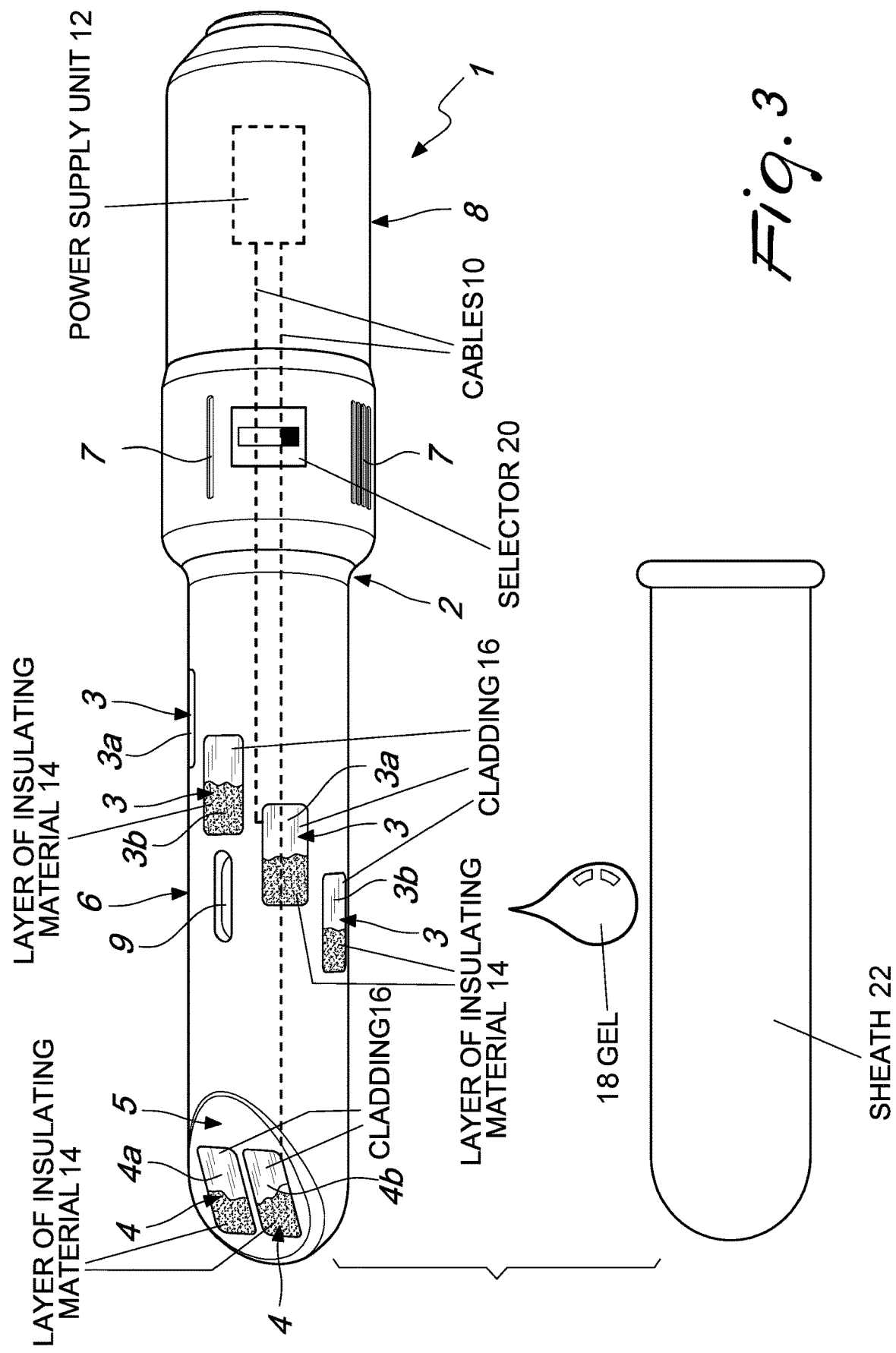
FIG. 3 is a schematic perspective view of the handpiece of FIGS. 1 and 2 with the sheath.

With reference to the figures, the numeral 1 generally designates a handpiece for intraorifice radiofrequency treatments.

The handpiece 1 comprises a substantially tubular body 2 which is provided with at least one emitter 3, 4 along its outer surface.

As seen in FIG. 3, the at least one emitter 3, 4 is connected, by means of adapted cables 10, to at least one power supply unit 12 provided with devices for the control and management of the electrical values transmitted to the at least one emitter 3, 4.

It is specified that the tubular body 2 of the handpiece according to the disclosure can conveniently be made of dielectric material.

Advantageously, the handpiece 1 according to the disclosure can comprise at least two distinct emitters 3, 4 distributed on the outer surface of the tubular body 2.

Each one of the emitters 3, 4 validly comprises at least one electrode which is surmounted by a layer made of insulating material 14 constituted by the dielectric element of a ceramic capacitor.

It is specified that in electrical engineering the capacitor is a component which, in the ideal condition, can store indefinitely the accumulated charge and energy. In circuits operating in permanent sinusoidal conditions, the current that crosses an ideal capacitor is one quarter of a period in advance with respect to the voltage that is applied to its terminals.

If an electrical voltage is applied to the plates, the electrical charges separate and an electrical field is generated within the dielectric. The plate connected to the highest potential charges positively and the other one charges negatively. The positive and negative charges are equal and their absolute value constitutes the charge Q of the capacitor. The charge is proportional to the applied voltage and the proportionality constant is a characteristic of that particular capacitor that is known as electrical capacitance and is measured in farads:

$$C = Q/\Delta V$$

In other words, capacitance is equal to the ratio between the supplied electrical charge Q and the electrical voltage $\Delta V$. The capacitance of a planar capacitor (flat and parallel plates) is proportional to the ratio between the surface S of one of the plates and their distance d. The proportionality constant is a characteristic of the interposed insulator, is known as absolute electrical permittivity and is measured in farad/m.

The dielectric elements of ceramic capacitors are normally constituted by a pad made of ceramic material which has two metallized mutually opposite faces.

The dielectric element that will constitute part of the emitter 3, 4 in the handpiece 1 according to the disclosure instead has the metallization only on one of the two faces, so that the opposite face can come into contact with the skin of the patient, without subjecting said patient to any risk of electrical shock (or in general to exposure to the flow of a detectable electrical current).

It is specified that the dielectric element of a ceramic capacitor of the type used in the present application is constituted by materials chosen from is lead titanate-zirconate ($PbTi_xZr_{1-x}O_3$), barium titanate ($BaTiO_3$) and lead titanate ($PbTiO_3$), $ZnNb_2O_6$, $MgTa_2O_6$, $ZnTa_2O_6$, $(ZnMg)TiO_3$, $(ZrSn)TiO_4$, $Ba_2Ti_9O_{20}$, $MgNb_2O_6$, combinations thereof, and the like.

It is specified that the ceramic capacitor whose dielectric will be used in the handpiece 1 can be chosen preferably also among ceramic capacitors for high voltage (although this constructive choice is in no way limiting, since the use of dielectrics of ceramic capacitors adapted to any operating voltage is provided).

The list given above is not exclusive but is merely an indication of the type of materials that can be used to provide the emitter 3, 4 of the handpiece 1 according to the disclosure.

Furthermore, it is specified that the layer made of insulating material of the emitter 3, 4 constituted by the dielectric element of a capacitor can advantageously have a relative dielectric constant higher than 30.

This means that the materials used to provide the insulating layer of the emitters 3, 4 of the handpieces 1 according to the disclosure usefully can have an electrical permittivity that is at least 30 times higher than that of vacuum.

It is specified that the preferred values of relative dielectric constant actually can be even much higher, with values close to and higher than 100.

It should be pointed out that in handpieces 1 according to the disclosure the layer made of insulating material of the emitters 3, 4, constituted by the dielectric element of a ceramic capacitor, can favorably have a thickness comprised between 0.01 mm and 20 mm.

It is appropriate to point out that one surface of the ceramic element of each emitter 3, 4 comprises a cladding 16 made of a material with high electrical conductivity, which is electrically connected to the electrode for the delivery of a radiofrequency treatment of the capacitive type. The electrode receives a flow of electric power (appropriately modulated in order to optimize the treatment and make it suitable for the epithelial tissue on which the procedure is performed) by the power supply unit 12.

With particular reference to a constructive solution of unquestionable interest in practice and in application, the emitters 3, 4 can conveniently be a plurality.

In this case, they are validly distributed along the lateral surface of the tubular body 2.

In the constructive hypothesis that has just been described, it is also noted that the plurality of emitters 3 can be effectively distributed along the lateral surface of the tubular body 2 according to at least one spiral.

In this manner, the emitters 3 are mutually offset by a predefined angle (with respect to a reference of angular coordinates the origin of which lies on the longitudinal axis of the handpiece 1) and also by a predefined length (in a longitudinal direction).

A further possible constructive variation provides for the adoption of at least two emitters 3a, 3b or 4a, 4b which constitute pairs of terminals 3a, 3b or 4a, 4b which are mutually associated, for the execution of a capacitive radiofrequency treatment of the bipolar type within an anatomical cavity.

In capacitive radiofrequency treatments of the bipolar type, the flow of electric power (which follows the lines of force of the electrical field) exits from an emitter 3a, 4a (or 3b, 4b) and reenters the contiguous one 3b, 4b (or 3a, 4a).

This constructive solution is very valid, since it eliminates the need to connect the patient to a conducting plate in order to close the electrical circuit, as is instead necessary for monopolar capacitive radiofrequency treatments.

The advantageous consequence of this embodiment is the elimination of electrical currents along the body of the patient (between an emitter and the plate) which are typical of monopolar capacitive radiofrequency: in the case of bipolar capacity radiofrequency, the currents are extremely localized in the treatment area, maximizing the effects of the treatment and avoiding contraindications caused by the effects of the currents along the body of the patient (even very far from the area to be treated).

It is specified that according to the disclosure at least one emitter 4 can be arranged positively at a terminal portion 5 of the tubular body 2.

The emitter 4, arranged on the terminal portion 5, has the purpose of performing radiofrequency treatments on outer surfaces of epithelial tissue of the patient. In that case, the handpiece 1, gripped by the operator, is kept for predefined times with the portion 5 resting on the tissues to be treated (so that the at least one emitter 4 is in contact with them) in order to deliver the treatment.

It is specified that in this case it might be useful to arrange on the portion 5 (and therefore also on the at least one emitter 4) a predefined quantity of viscous gel 18 such as the one used in ultrasound devices, in order to maximize the effects of the treatment.

It is pointed out that, with particular reference to a constructive solution of unquestionable interest in practice and in application, the tubular body 2, at the terminal portion 5, can advantageously comprise a contoured surface for the accommodation of a pair of emitters 4a, 4b which are substantially arranged side by side and mutually associated for the execution of a capacitive radiofrequency treatment of the bipolar type on external anatomical surfaces.

In order to ensure that the radiofrequency treatments administered means of the handpiece 1 according to the disclosure are safe and effective, the at least one power supply unit 12 favorably comprises a selector 20 for the alternating and not simultaneous operation of the emitters 3 (3a, 3b in the case of a bipolar arrangement) distributed on the lateral surface of the tubular body 2 and of the at least one emitter 4 (4a, 4b in the case of a bipolar arrangement) located on the terminal portion 5 of the tubular body 2.

The protection of the present disclosure also extends to a kit for the execution of intraorifice radiofrequency treatments which comprises: the handpiece 1 in any one of the embodiments described so far; a viscous gel 18 of the type of those used with ultrasound devices such as ultrasonic imagers (or more generically for Doppler ultrasonography, ultrasonic imaging, physio-kinesiotherapy, electroencephalography, electromyography, and the like); a thin sheath 22 whose shape and dimensions are complementary to a distal part 6 of the handpiece 1.

Prior to the use of the handpiece 1, the corresponding distal part 6 must be coated uniformly with the viscous gel and covered with the sheath.

In this manner, during the capacitive radiofrequency treatment only the sheath makes contact with the epithelial tissue of the anatomical cavity in which the treatment will be performed.

The handpiece 1 will make contact exclusively with the viscous gel and therefore any possibility of cross-contagion among different patients will be avoided.

Conveniently, the sheath can be made of a material of a type chosen preferably among polymers, elastomers and the like.

The use of a sheath made of dielectric material allows to provide a barrier against any contamination by contact but allows the electrical coupling of the bipolar emitters 3a, 3b and 4a, 4b.

In order to eliminate any possibility of contagion among different patients, the sheath is advantageously of the disposable type: upon each treatment, a new sheath constitutes a cladding for the handpiece 1 in order to prevent contact thereof with the epithelial tissue subjected to the treatment and, the end of each treatment, said used sheath is discarded in the trash.

It is specified that in order to simplify the execution of the treatment of an anatomical cavity (for example for the rejuvenation of the epithelial tissue of the vagina), the handpiece 1 can positively comprise references 7 that are present on the corresponding handle 8 with a predefined angular distribution.

The presence of the references 7 allows the operator to arrange the is distal part 6 of the handpiece 1 (appropriately coated with viscous gel and covered with a corresponding new sheath) in the anatomical cavity, having a first reference 7 in a preset position, and allowing the treatment to continue (with the handpiece 1 fixed in this position) for a predefined time.

When the time interval expires, the operator must rotate the handpiece 1 until the next reference 7 is aligned with the predetermined position and leave it for a predefined time interval.

In this manner, at the end of the of a full turn of the handpiece 1 about itself (which can be detected since the first reference returns to the predetermined position), the treatment will be completed and all the surfaces of the anatomical cavity will have been affected by a complete capacitive radiofrequency treatment.

The spiral distribution of the emitters 3 along the lateral surface of the distal portion 6 of the handpiece 1 in fact allows to arrange said emitters 3 so that they face every part of the anatomical cavity within one turn of the handpiece 1 about itself.

Advantageously, the present disclosure solves the problems described previously, proposing a handpiece 1 for radiofrequency intraorifice treatments which avoids phenomena of cross-contamination among multiple patients and is therefore very hygienic and safe.

The use of disposable sheaths for the covering of the handpiece 1, which therefore ensures that said handpiece 1 never makes contact with the epithelial tissue and with the mucous membranes of the patient, in fact allows to eliminate risks of contagion and/or contamination.

Furthermore, this solution allows to avoid resorting to the sterilization of the handpiece 1 after each treatment, since it only makes contact with sterile material (such as the viscous gel and the sheath).

Conveniently, the handpiece 1 according to the disclosure does not require the presence of expensive components to be replaced at each treatment.

Since sterilization of the parts that make contact with the epithelial tissue or with the mucous membranes of the patient is not required (as the handpiece 1 never makes contact with them), it is not necessary for some components of the handpiece 1 to be detachable in order to be subjected to sterilization.

Usefully, the handpiece 1 does not require means for cooling the component that supplies current with the correct electrical parameters to the head.

It is in fact sufficient to provide control of the treatment temperature (in order to avoid overheatings of the emitters 3, 4), which might provide for a reduction (adjustment) of the intensity of the generated electrical field, whereas any device intended for cooling and in general to remove heat from any component of the handpiece 1 is entirely absent.

For this reason, the handpiece 1 is simpler than those of the known type and is therefore less subject to breakage, furthermore requiring less and simpler maintenance than those of the known type.

Efficiently, therefore, the handpiece 1 according to the disclosure is in practice scarcely subject to malfunctions, indeed in relation to the minimal number of components that constitute it, and is therefore extremely reliable.

Positively, the handpiece 1 according to the disclosure is characterized by a very simple use, being easily usable even by operators who are not specifically trained but are professionally authorized.

The presence of the references 7 on the handle 8 and the presence of the selector which alternately excludes the emitters 3 and the emitters 4 simplifies the methods of administration of the treatment and minimizes the risk of making mistakes on the part of the operator.

Validly, the handpiece 1 for intraorifice radiofrequency treatments is very simple to be provided in practice, also entailing substantially low costs: these characteristics make the handpiece 1 according to the disclosure an innovation of certain application.

The disclosure thus conceived is susceptible of numerous modifications and variations, all of which are within the scope of the accompanying claims; all the details may furthermore be replaced with other technically equivalent elements.

The adoption of a temperature sensor 9 is provided, in order to check at all times the temperature of the epithelial tissue subjected to the treatment, so as to verify that it is performed in an optimum manner.

All the remarks made above are to be considered valid and extendable also in the case in which the handpieces 1 according to the disclosure and the corresponding kit are used to subject the patient to medical treatments intended for the treatment of pathologies of the urogenital system.

In the exemplary embodiments shown, individual characteristics, given in relation to specific examples, may actually be interchanged with other different characteristics that exist in other exemplary embodiments.

In practice, the materials used, as well as the dimensions, may be any according to the requirements and the state of the art.

The invention claimed is:

1. A handpiece for intraorifice radiofrequency treatments comprising a substantially tubular body provided with at least one emitter along an outer surface thereof, said at least one emitter being connected by cables to at least one power supply unit provided with devices for the control and management of electrical values transmitted to said at least one emitter, and further comprising, distributed on the outer surface of the tubular body that is entirely made of dielectric material, a plurality of emitters which comprise at least one electrode surmounted by a layer of insulating material constituted by a dielectric element of a ceramic capacitor, the dielectric element of each emitter being a ceramic element having one surface comprising a cladding made of a material with high electrical conductivity which is electrically connected to said electrode in order to deliver a radiofrequency treatment of the capacitive type, wherein said plurality of emitters are distributed along a lateral surface of said tubular body according to at least one spiral.

2. The handpiece according to claim 1, wherein said plurality of emitters constitute pairs of mutually associated terminals for performing a capacitive radiofrequency treatment of the bipolar type inside an anatomical cavity.

3. The handpiece according to claim 1, wherein at least one emitter is arranged at a terminal portion of said tubular body.

4. The handpiece according to claim 3, wherein said tubular body, at said terminal portion, comprises a contoured surface for accommodation of a pair of emitters which are arranged substantially side by side and mutually associated for executing a capacitive radiofrequency treatment of the bipolar type on external anatomical surfaces.

5. The handpiece according to claim 3, wherein said at least one power supply unit comprises a selector for an alternating and not simultaneous operation of said emitters distributed on the lateral surface of said tubular body and of said at least one emitter arranged on said terminal portion of said tubular body.

6. A kit for the execution of intraorifice radiofrequency treatments, the kit comprising:
    a handpiece according to claim 1;
    a viscous gel of the type used with ultrasound devices such as ultrasonic imagers;
    a thin sheath whose shape and dimensions are complementary to a distal part of said handpiece;
    prior to the use of said handpiece, said distal part being coated uniformly with said viscous gel and covered with said thin sheath, which will make contact with the epithelial tissue of an anatomical cavity in which the treatment will be performed.

7. The kit according to claim 6, wherein said sheath is made of a material chosen from at least polymers and elastomers.

8. The kit according to claim 6, wherein said sheath is disposable, at each treatment, a new sheath constituting a cladding for said handpiece to prevent the contact thereof with the epithelial tissue subjected to the treatment and, at the end of each treatment, said used sheath is discarded in the trash.

* * * * *